United States Patent [19]
Helle et al.

[11] Patent Number: 5,400,804
[45] Date of Patent: Mar. 28, 1995

[54] METHOD AND AN EQUIPMENT FOR INSTALLING A MEDICINE CAPSULE ON A SUPPORT

[75] Inventors: Timo Helle; Rolf Hartzell, both of Turku; Pekka Nieminen, Preitilä ; Pekka Lankinen, Turku, all of Finland

[73] Assignee: Leiras Oy,, Turku, Finland

[21] Appl. No.: 93,893

[22] Filed: Jul. 20, 1993

[30] Foreign Application Priority Data

Jul. 31, 1992 [FI] Finland ................................. 923467

[51] Int. Cl.$^6$ .......................... A61B 19/00; A61F 6/06
[52] U.S. Cl. ...................................... 128/898; 128/830
[58] Field of Search ................... 128/830–841

[56] References Cited

U.S. PATENT DOCUMENTS

| | | | |
|---|---|---|---|
| 3,323,511 | 6/1967 | Holter | 128/840 |
| 3,507,274 | 4/1970 | Soichet | 128/840 |
| 3,509,877 | 5/1970 | Weiss | 128/840 |
| 4,949,732 | 8/1990 | Spoon | 128/840 |
| 4,993,432 | 2/1991 | Shields | 128/838 |

Primary Examiner—Michael A. Brown
Attorney, Agent, or Firm—Adduci, Mastriani, Schaumberg & Schill

[57] ABSTRACT

The invention relates to a method and an equipment for inserting a tubular medicinal capsule on a support. In accordance with the invention, the opening extending through the capsule is expanded by blowing pressurized air into the opening immediately ahead the support being inserted into the opening. After the capsule has entered into its position, the pressurization is relieved, whereby the capsule opening contracts and locks the capsule on the support.

2 Claims, 5 Drawing Sheets

Fig.3
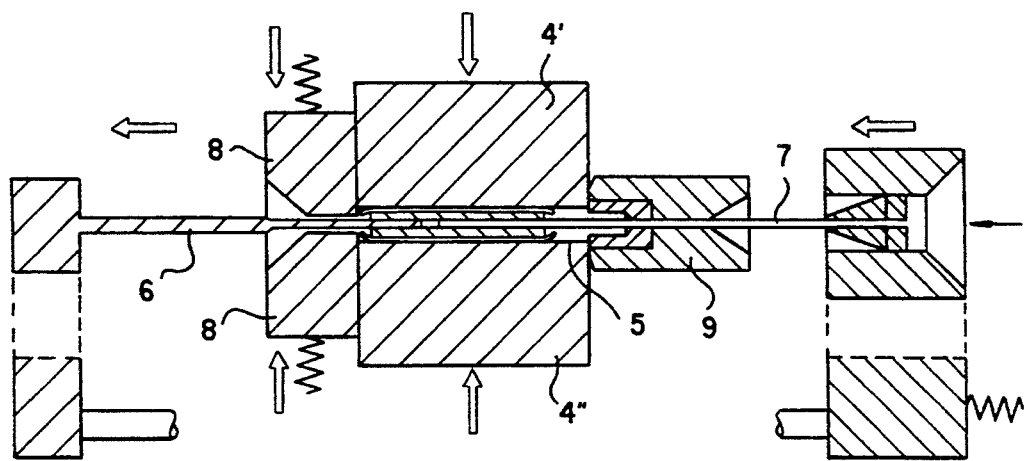
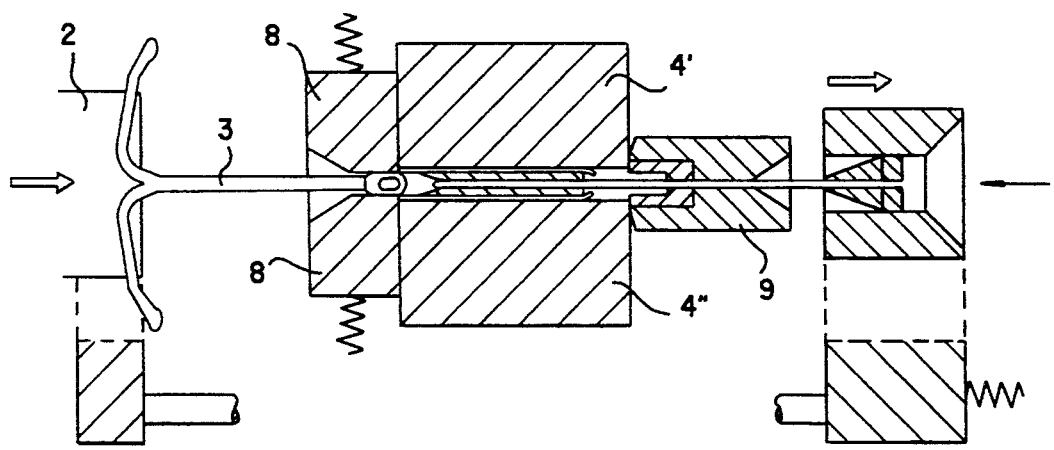
Fig.4

METHOD AND AN EQUIPMENT FOR INSTALLING A MEDICINE CAPSULE ON A SUPPORT

BACKGROUND OF THE INVENTION

The present invention relates to a method and an equipment for installing a tubular medicinal capsule on a support. The medicinal capsule concerned may be, e.g., a capsule releasing a contraceptive subtance, and which is installed on a suitable support for fixing the capsule inside the womb. Such contraceptive means are known per se and manufactured in different ways. In these, the support is formed from an anchor-like element of an inert substance, on whose arm the hollow tubular medicinal capsule is installed.

It it known to install such a tubular medicinal capsule on the support by swelling of the capsule in a suitable solvent and thereafter inserting the capsule in its swollen state on the support. The capsule shrinks as the solvent evaporates, and consequently becomes fastened on the support.

SUMMARY OF THE INVENTION

In the equipment according to the invention, a different principle is followed. This principle is based on the expansion of the capsule by an internal pressure to such a state that the support may be inserted inside it. When the pressure has been relieved, the capsule then returns towards its initial state and becomes fastened on the support. The characteristic features of the method and equipment according to the invention appear from the enclosed claims.

BRIEF DESCRIPTION OF THE DRAWINGS

The invention is described by means of the accompanying drawings, in which

FIG. 3 shows the equipment in an installation step, where the medicinal capsule is in a closed connecting mold;

FIG. 4 shows the equipment in an installation step, where the support is in the initial state of the installation step;

DESCRIPTION OF THE PREFERRED EMBODIMENT

Figure 1:
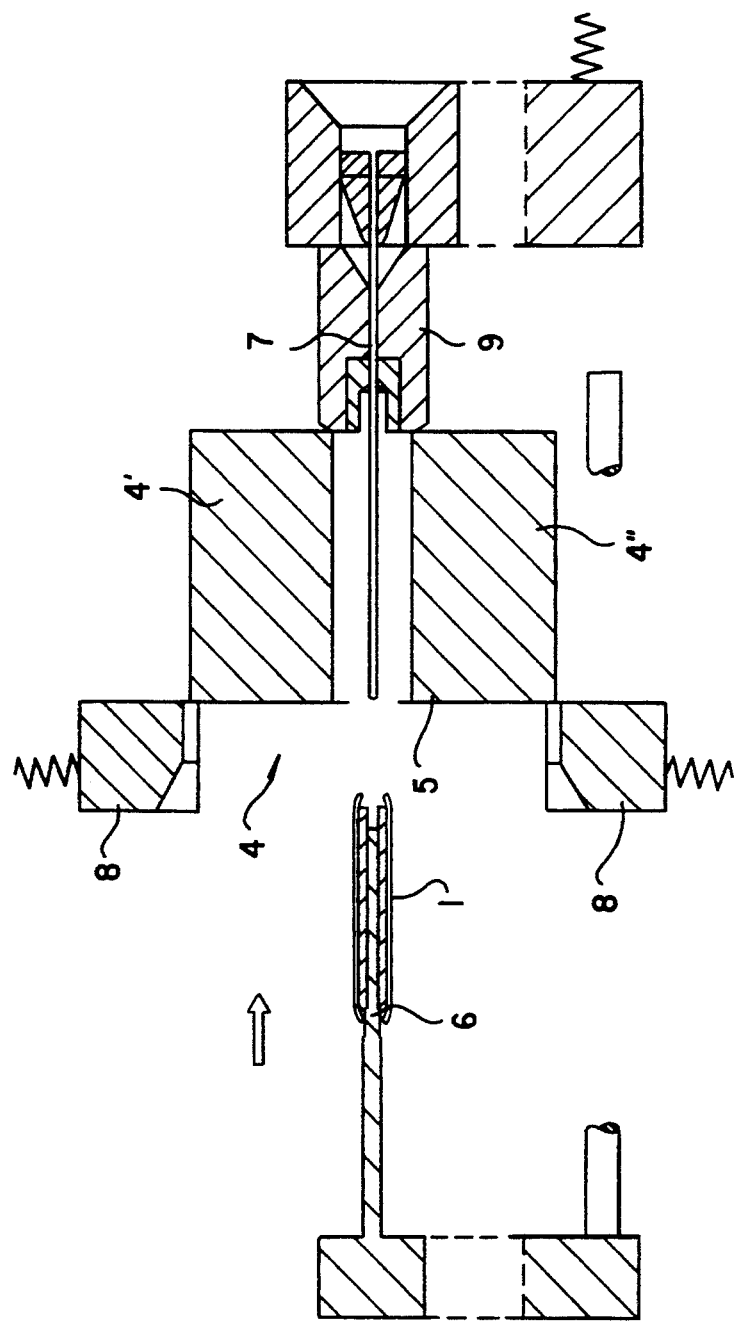
FIG. 1 shows the device of the subject invention in the initial step of the installation of a medicinal capsule.
Figure 2:
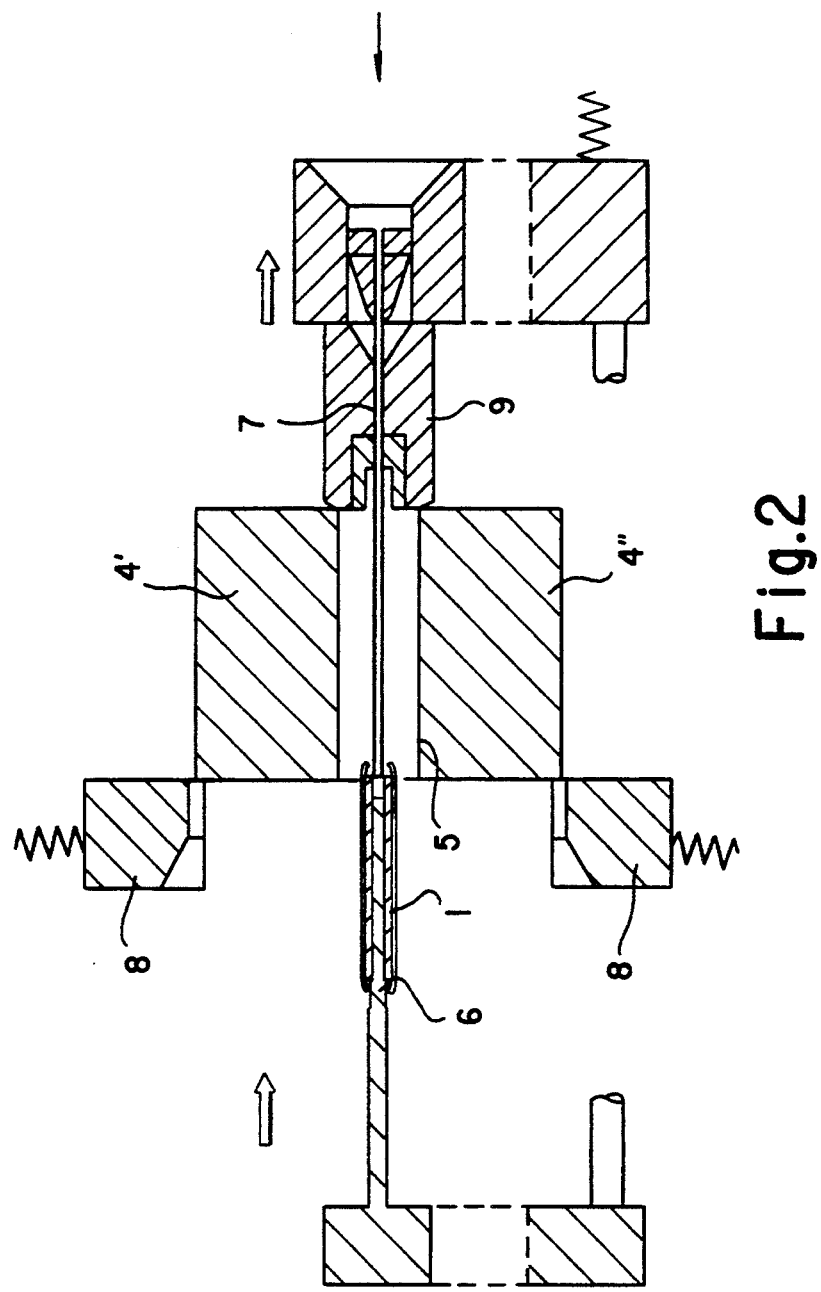
FIG. 2 shows the next step of the operating cycle of the installation.

FIG. 1 shows the basic parts of the inventive equipment in the initial step of the installation cycle. A connecting mold or housing 4 is in its open position and a pressure needle 7 is inserted in an opening 5 of the mold prepared to receive a capsule 1, which is brought to the connecting mold on a mandrel 6, when the mold is open. When the capsule supported by the mandrel and the pressure needle meet at the mouth of the opening of the mold, the pressure needle starts a withdrawal movement. After this, the mandrel 6 and the capsule 1 thereon as well as the pressure needle located against the end of the capsule continue their movement in a direction, where the capsule advances into the open mold.

When the capsule has totally entered into the connecting mold, the situation is as shown in FIG. 3, i.e., the mold is closed and the mandrel 6 has started its return movement. At the same time, the pressurized needle 7 follows the mandrel inside the capsule, and expands then the capsule by means of air discharging from the openings at the needle tip, and thereby helps the removal of the mandrel. After the mandrel has left the capsule and the pressure needle has reached the end of the capsule, a support 3 on which the capsule is to be installed is brought to the end of the capsule, from which the mandrel has been removed, as shown in FIG. 4.

Figure 5:
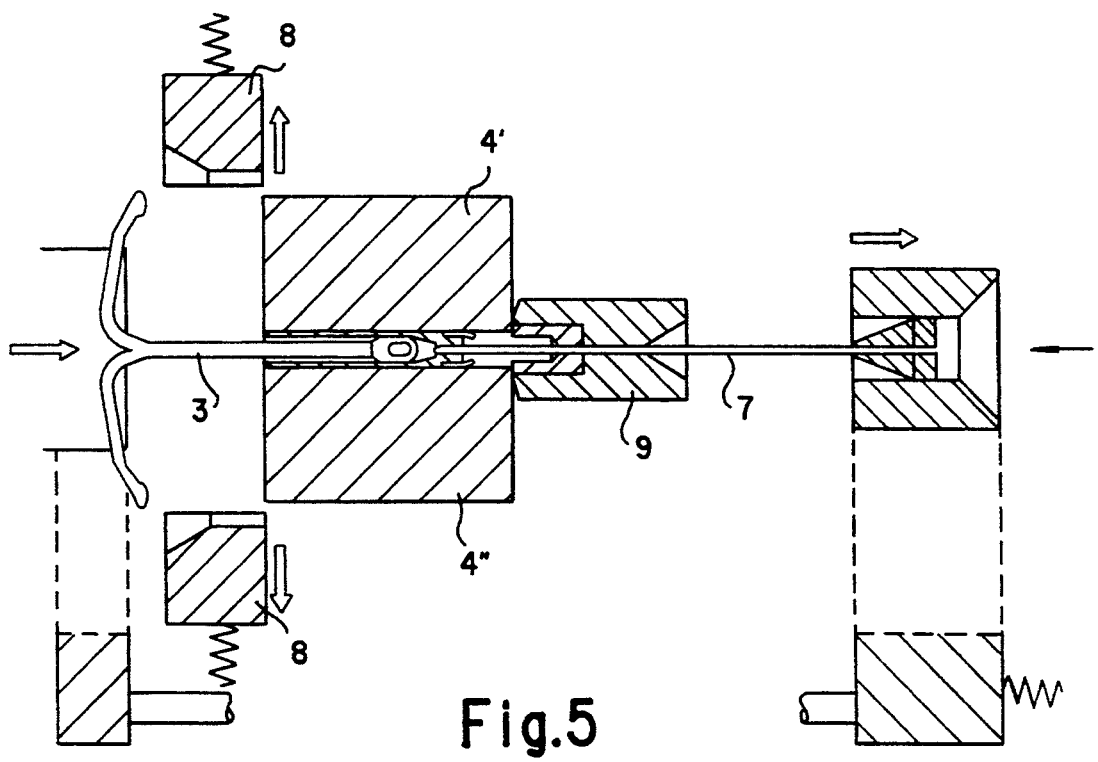
FIG. 5 shows the equipment in the final step of the installation.
Figure 6:
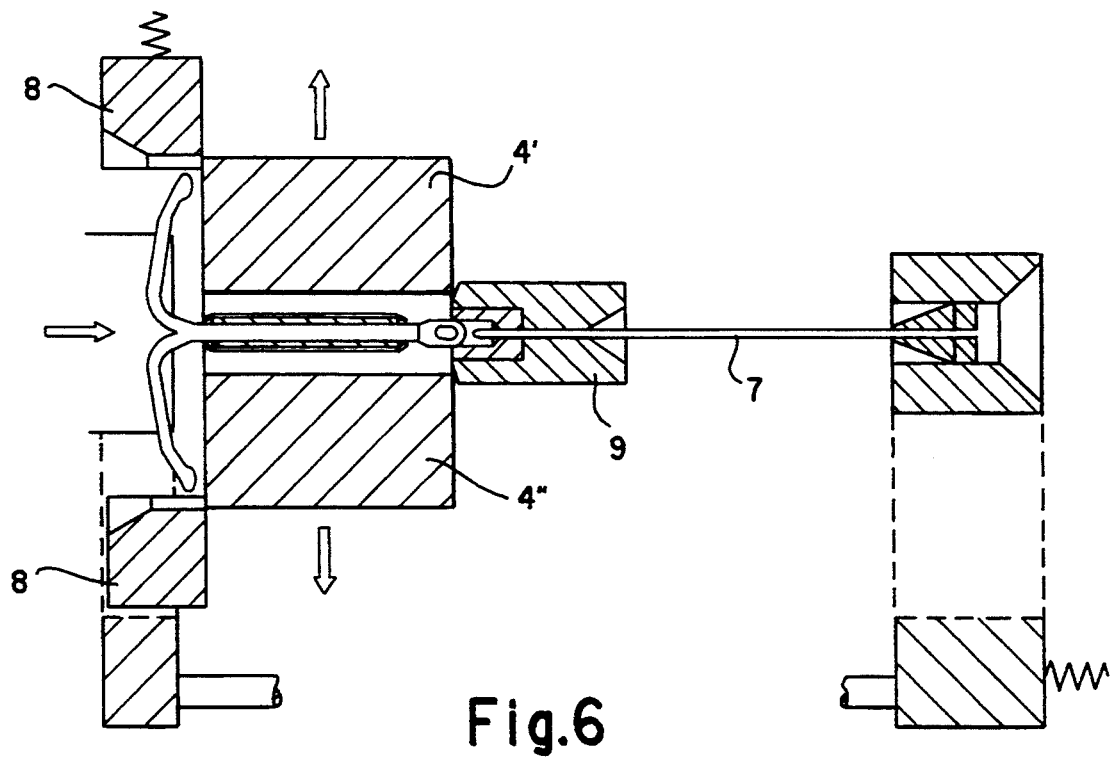
FIG. 6 shows the equipment after the installation has been completed.
Figure 7:
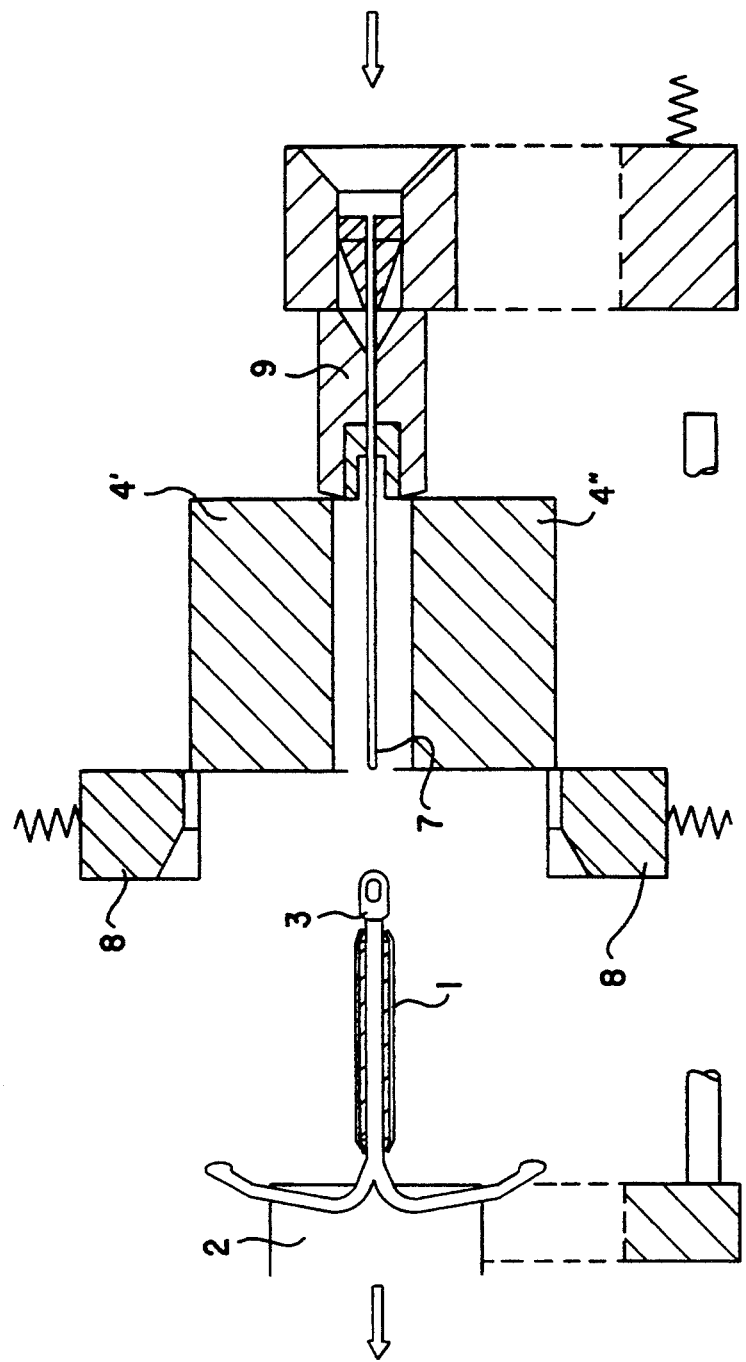
FIG. 7 shows the equipment in the removal step of the ready product.

After this, the support 3 is pushed inside the capsule to follow the pressurized needle 7 expanding the capsule when escaping ahead the support, as shown in FIGS. 5 and 6. When the support has been pushed to an accurate position in the capsule, the connecting mold is opened and the ready product is removed. The pressure needle is pushed to the opened mold, and the operating cycle is started from the beginning according to FIG. 1.

The equipment described also includes two guides 8, 9 on both sides of the connecting mold 4, which help the operation by guiding on one hand the movements of the mandrel 6 and on the other hand the movements of the pressure needle 7. However, these guides are not essential, if the movements of said parts and the tightness of the operation can be ensured by other means.

The cross-sectional form of the opening 5 of the connecting mold 4 is preferably selected to be compatible with the cross-sectional form of the support 3.

For controlling the correct mutual operation of the equipment parts, the equipment naturally includes an electric control system, whose detailed construction and operation are well known to those skilled in the art, and they do not form an essential part of the present invention.

We claim:

1. A method for installing a tubular medicinal capsule having an opening extending through on a support, comprising expanding the opening extending through the capsule by pressurizing the opening immediately ahead of the support being inserted into the opening, and thereafter fastening the capsule on the support by relieving the expanding pressure.

2. A device for mounting a medicinal capsule provided with a through-opening on a support rod, the device comprising:

a connecting mold, provided with a through-opening and dividable into two parts relative to at least one plane through the opening, the opening having a length exceeding a length of the capsule to be mounted;

a mandrel insertable into the opening of the connecting mold and removable therefrom at one end of the opening, said mandrel having an outer diameter substantially equal to an inner diameter of the capsule to be mounted, and a length substantially equal to the length of the capsule to be mounted;

a pressure needle insertable into and removable from the opening of the connecting mold at an end opposite to an inlet end of the mandrel, the pressure needle having an open tip with an outer diameter substantially equal to an inner diameter of the capsule;

means for inserting the support rod into and withdrawing the support rod from the connecting mold opening from the same end as the mandrel;
control means for controlling operation of the parts of the connecting mold, the mandrel, the pressure needle and insertion devices of the support; and
pressure means for pressurizing the pressure needle.

* * * * *